United States Patent [19]

Rosenthal

[11] Patent Number: 4,742,581

[45] Date of Patent: May 10, 1988

[54] COOLING BAND SYSTEM

[76] Inventor: Daniel H. Rosenthal, 222 N. Pompano Blvd., Pompano Beach, Fla. 33062

[21] Appl. No.: 848,638

[22] Filed: Apr. 7, 1986

[51] Int. Cl.$^4$ ............................................. A42C 5/00
[52] U.S. Cl. ........................................ 2/181; 2/171; 2/170
[58] Field of Search ............... 2/170, 171, 181, 181.6, 2/181.2, 182.8; 128/380; 604/378, 383

[56] References Cited

U.S. PATENT DOCUMENTS

| | | | |
|---|---|---|---|
| 1,633,586 | 6/1927 | Hunter | 2/170 X |
| 1,907,709 | 5/1933 | Barrow | 2/171 |
| 2,160,567 | 5/1939 | Sterne | 2/171 |
| 2,223,332 | 11/1940 | Sterne | 2/171 |
| 2,783,474 | 3/1957 | Campagna et al. | 2/171 |
| 2,832,077 | 4/1958 | McGinnis | 2/171 |
| 3,466,664 | 9/1969 | Militello | 2/171 |
| 4,502,156 | 3/1985 | Wishman | 2/181 |

Primary Examiner—Werner H. Schroeder
Assistant Examiner—Judith L. Olds

[57] ABSTRACT

A head or wrist sweatband including united sheet sublayers of foraminous heat conductive foraminous and moisture absorbant fabrics, for immersion in tap water at room temperature, functioning to evaporate the water with concurrent cooling of the human body and absorption of perspiration. The inner surface of the band is comprised of said heat conductive foraminous fabric first sublayer and in use is adjacent the skin of the wearer. Said moisture absorbant second sublayer is connected in interfacial association upon said first sublayer and forms the outer surface of said band. In use, the band is initially immersed in room temperature water and placed upon the user. Heat from the body of the user raises the temperature of the first sublayer which in turn raises the temperature of the second sublayer causing evaporation and consequent cooling of the band. Perspiration from the user is absorbed by the second sublayer for continous evaporation and cooling.

8 Claims, 1 Drawing Sheet

4,742,581

COOLING BAND SYSTEM

FIELD OF INVENTION

This invention relates to a cooling band system in the form of a headband or wristband laminate of at least one layer of fiberglass or metal mesh and at least one layer of cotton.

DESCRIPTION OF PRIOR ART

It is well known to absorb perspiration from the skin of a human by wearing a cloth covered band. It is also well known to use a laminated fabric to interpose a thermal barrier so as to protect a wearer from cold climates. Such a laminate is disclosed in U.S. Pat. No. 4,569,874 and includes a core layer of hollow fibers acting as a thermal blanket sandwiched between inner and outer skins for the stated purpose of minimizing the dissipation of body heat and also extracting heat from the sun.

SUMMARY OF THE INVENTION

The present invention utilizes a laminate comprised of an air-pervious mesh or foraminous sheet-like first sub-layer of heat-conductive material covered by a sheet like air pervious moisture absorbant second sublayer of approximately the same size, which may be a woven 100% cotton fabric connected in interfacial association and formed into an endless band. In use, the composite laminated band is immersed in water and placed upon the wearer. The first sublayer is in interfacial or spaced facial relation to the skin, the second sublayer being interfacially connected to the outer surface of said first sublayer. As the body temperature of the wearer increases, so too will the temperature of the band, causing evaporation of the liquid within the second sublayer. As the user's body temperature rises further, heat will be convected away from the skin causing a coincident increase in the temperature of the heat-conductive second sublayer. At the same time, moisture in the form of sub-cooled liquid water and water vapor is absorbed by the first sublayer, keeping that sublayer wetted. Because evaporation is a cooling process, evaporation from said second sublayer into the adjacent atmosphere will cause a decrease in the temperature of said second sublayer. Correspondingly the heated first sublayer, being denser than the second sublayer, will give off heat to said second sublayer, causing a further temperature increase in said second sublayer and corresponding evaporation therefrom. This continuous process of extracting heat from the body and dissipating it results in the advantages of inter alia, lowering body temperature and enhancing the user's comfort. The band can be in the form of a headband or wristband. The band includes an outer layer of material such as cotton and an inner mesh or screen layer of fiberglass or metal.

It is the principal object of this invention to provide a cooling band system for lowering the body temperature of its wearer.

It is another object of this invention to provide a cooling band system comprised of laminated endless band utilizing the mechanisms of conduction and convection.

It is yet another object of the invention to fabricate a head or wristband including an outer fabric and an under layer of screen or mesh material which eliminates discomfort and personal annoyance of excessive sweating by providing a cooling means without adversely affecting the normal functions of the human body.

It is still another object of the invention to fabricate a head or wristband capable on immersion in room temperature drinking water for permitting evaporation of the water with concurrent cooling of the human body and absorption of perspiration by a band having an outer layer of material and an under layer of mesh or screen material.

Still other objects of the invention will be readily apparent to those skilled in the art in light of the following detailed description of the invention.

DETAILED DESCRIPTION OF THE PREFERRED EMBODIMENT

Figure 1:
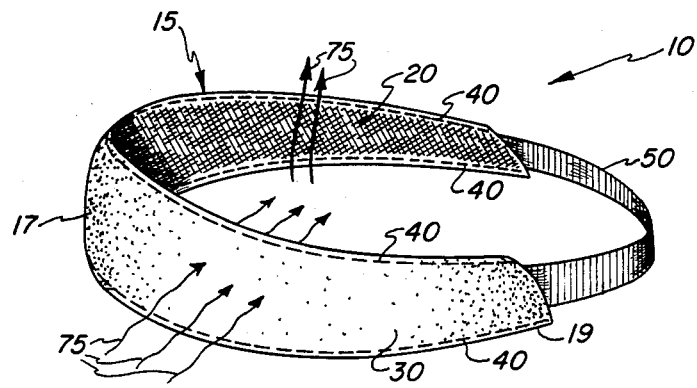
FIG. 1 illustrates a headband consistent with the invention.

Referring to FIG. 1 of the drawing, numeral 10 generally depicts a cooling band system in the form of a headband portion 15 and strap 50. The headband portion 15 includes an air pervious lower mesh or screen first sublayer composite 20 which is heat conductive united to an air pervious moisture absorbant second sublayer 30 by cotton thread 40. The free ends of the band portion 15 may be connected by an elastic band 50 or other connection arrangements. As illustrated in FIG. 1, band portion 15 has a greater width and area which is in contact with the head than at the rear 19 thereof and preferably, but not by way of limitation, constitutes at least four-fifths of the length of the band.

Figure 2:
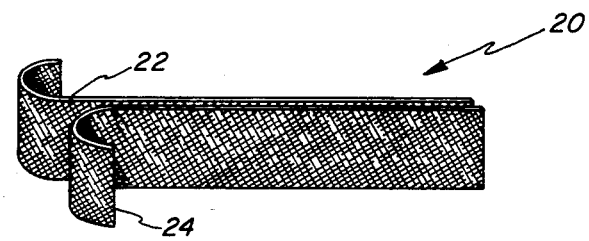
FIG. 2 illustrates a partial view of a first sublayer of heat conductive material of a composite sweatband of the invention.
Figure 4:
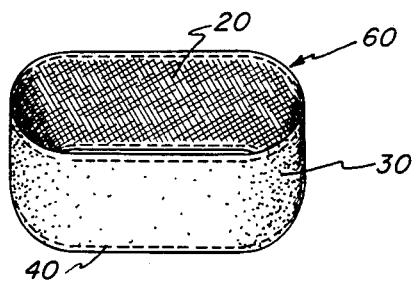
FIG. 4 illustrates a wristband laminate of the invention.

The first sublayer 20 as illustrated in FIGS. 2 and 4 may include a plurality of heat conductive sheet-like metal, fiberglass or other foraminous materials 22, 24 in interfacial back-to-back relationship. One or more layers of screen or mesh may be used. The materials utilized may be a foraminous sheet of copper or steel of high heat conductivity or a fiberglass material in the form of a screen or mesh or perforated sheet material. The sheets include apertures having a diameter greater than the apertures in the material portions 20. A 20-20 fiberglass screen may be used. The total open area of the foraminous sublayer 30 may be approximately 70% of the total area of layer 30. The second sublayer 30 also may be formed of woven fiberglass.

In one embodiment, generally rectangular stripes of sublayers 20 and 30 of generally equal length and width are interfacial contact and stitched together along or near the outermost edges and are generally formed in the shape of an endless band or loop with the first sublayer 20 forming the inner facing side and the second sublayer 30 forming the outer facing side. A length of elastically resilient band may be interposed within said loop or band to facilitate wearing and removal. From this embodiment it can be seen that the first sublayer 20 is closest the user's skin when worn and the second sublayer 30 connected to the outer facing side of sublayer 20. In this way, heat conducted away from the skin increases the temperature of first sublayer 20 through the heat transfer mechanism of convection and/or conduction. Said temperature increase causes a proportionate increase in the temperature of second sublayer 30, causing evaporation to occur. Because evaporation is a cooling process, the temperatures of both sublayers 20 and 30 will be lowered. This will cause an even greater temperature gradient to exist between the user's skin and the first sublayer 20, causing further cooling of the user. Continual evaporation is provided through perspiration from the user being absorbed by sublayer 30. Two layers of the screen material 22 and 24 are used to increase the time that the second sublayer 30 can retain water placed in the layer 30. Also the double first sublayer 20 allows more water to be held by the band as does the double layer of cotton 32 and 34.

Figure 3:
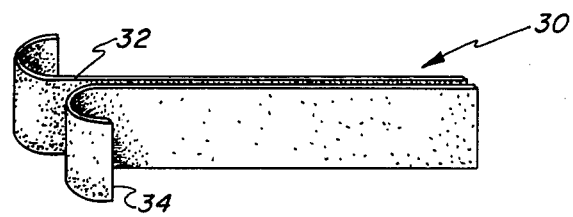
FIG. 3 illustrates a partial view of a second sublayer of air permiable material of the composite sweatband of the invention; respectively.

Referring to FIG. 3 the second sublayer 30 may include a pair of pieces of 100% sheet cotton 32, 34 in interfacial contact of the thickness of a conventional sweatband. A towel type of weave may be utilized. The cotton sheet or sheets may be of a greater thickness than the foraminous mesh.

Sublayers 20 and 30 may also be united by a cotton thread 40 to form a wristband 60 as illustrated in FIG. 4. The headband may be in the same form as the wristband but having a larger diameter.

An important aspect of this invention is avoidance of direct contact of the entire second sublayer 30 with the skin surface of the user which would adversely affect the rate of flow of an air stream 75 by plugging the foramina in the first sublayer 20. To this end, therefore, the sublayers 20 and 30 may be united solely by threads using a sewing technique utilizing parallel stitching 40 as shown in FIG. 1 contiguous to the sides of the interfacially connected sublayers. Connecting the respective sublayers in this way allows a free flow of air to surround both of said sublayers for the most efficient heat transfer away from the user's skin.

METHOD OF USE

The cooling band 10 is initially immersed in room temperature tap water and then placed upon the user, such as around the heat or wrist. Normal evaporation of the moisture in moisture absorbant sublayer 30 lowers the temperature of the cooling band. Heat from the skin is transferred to first sublayer 20. As said sublayer 20 increases in temperature, second sublayer 30 is heated, causing further evaporation therefrom. Absorption of perspiration by second sublayer 30 maintains an acceptable degree of moisture therein for continuous evaporation therefrom resulting in heat transfer away from the wearer's skin.

As illustrated in FIG. 1, air 75 circulating through the moist material of sublayer 30 penetrates to the foraminous sublayer 20 in contact with the skin and the air causes convective heat transfer resulting in augmenting sweat evaporation with concurrent cooling of the wearer's skin.

The wrist sweatband 60 of FIG. 4 functions similarly to forehead sweatband 10 of FIG. 1.

It should be noted that entire articles of clothing, including such items as would cover substantial portions of the body, are contemplated by this invention and said invention is not limited to bands alone.

It is evident from the above disclosures that modifications of the invention are within the scope thereof without departing from the spirit of the invention or sacrificing the principle advantages thereof.

What is claimed is:
1. A laminated cooling band for a person comprising:
   (a) an air pervious heat conductive first sublayer of a screen of a foraminous glass fabric;
   (b) an air pervious fabric second sublayer of cotton fabric, said cotton fabric is a moisture absorbent material; and
   (c) uniting means for connecting said first sublayer and second sublayer in interfacial contact, said uniting means rendering said first and second sublayers in separably pliable interfacial association but for said uniting means uniting said sublayers into said cooling band;
   said first and second sublayers being free of substances affecting the porosity of said glass fabric and said cotton fabric subassemblies and resultant air passage therethrough;
   said first sublayer and second sublayers have peripheral edges and are joined at their edges using said uniting means, said edges are aligned, said uniting means being generally arranged parallel to the aligned said edges and closely spaced therefrom; said peripheral edge of said heat conductive first sublayer is exposed to the atmosphere; said laminated cooling band forms part of a cooling band system in the form of an endless loop for lowering the body temperature of a wearer, said first sublayer is the inner surface means for skin contact, said second sublayer comprising the outer surface means for holding water for evaporative cooling.

2. A laminated cooling band for a person as recited in claim 1 wherein said uniting means is cotton thread.

3. A laminated cooling band for a person as recited in claim 1 wherein said second sublayer is 100% cotton.

4. A laminated cooling band as recited in claim 1 wherein said laminate portion constitutes at least four-fifths of the length of said band and said remaining portion comprises the rest of said endless loop.

5. A laminated cooling band as recited in claim 4 wherein said band is a head sweatband.

6. A cooling band as recited in claim 4 wherein said band is a wrist sweatband.

7. A laminated cooling band for a person comprising:
   (a) an air pervious heat conductive first sublayer of a foraminous metal screen fabric forming an inner surface means for skin contact;
   (b) an air pervious fabric second sublayer of cotton fabric forming an outer surface means for holding water for evaporative cooling; and
   (c) uniting means for connecting said first and second sublayers in interfacial contact, said uniting means rendering said first and second sublayers in separably pliable association but for said uniting means uniting said sublayers;
   said first and second sublayers being free of substances affecting the porosity of said fabric subassemblies and resultant air passage therethrough;
   said first sublayer and second sublayers have peripheral edges and are joined at their edges using said uniting means, said edges are aligned, said uniting means being generally arranged parallel to the aligned said edges and closely spaced therefrom; said peripheral edge of said heat conductive first sublayer is exposed to the atmosphere.

8. A laminated cooling band as recited in claim 7 wherein said second sublayer is 100% cotton.

* * * * *